United States Patent

Bouillon et al.

[11] 3,956,352
[45] May 11, 1976

[54] HETEROCYCLIC ALUMINUM COMPOUNDS AND PROCESS FOR THEIR PREPARATION

[75] Inventors: Claude Bouillon, Eaubonne; Pierre Dufaure, Paris; Georges Rosenbaum, Asnieres, all of France

[73] Assignee: L'Oreal, Paris, France

[22] Filed: Dec. 28, 1973

[21] Appl. No.: 429,070

[30] Foreign Application Priority Data
Jan. 2, 1973  Luxemburg............................ 66783

[52] U.S. Cl. ........................... 260/448 AD; 424/47; 424/68
[51] Int. Cl.$^2$ ........................................... C07F 5/06
[58] Field of Search .............................. 260/448 AD

[56] References Cited
UNITED STATES PATENTS

| | | | |
|---|---|---|---|
| 3,082,235 | 3/1963 | Stamm .......................... | 260/448 AD |
| 3,410,856 | 11/1968 | Harris et al. ............. | 260/448 AD X |
| 3,444,226 | 5/1969 | Schmank et al. ............ | 260/448 AD |
| 3,686,249 | 8/1972 | Hartmann .................... | 260/448 AD |
| 3,819,671 | 6/1974 | Bouillon et al............... | 260/448 AD |

OTHER PUBLICATIONS

Mehrotra et al., Jour. Indian Chem. Soc., Vol. 39, No. 9, pp. 635–640, (1962).

*Primary Examiner*—Helen M. S. Sneed
*Attorney, Agent, or Firm*—Cushman, Darby & Cushman

[57] ABSTRACT

A heterocyclic aluminum compound of the formula

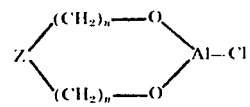

wherein $n$ is 1 or 2. When $n$ is 1, Z is —CH=CH—. When $n$ is 2, Z is either —(CH$_2$)$_m$ wherein $m$ is 0–6, or a heteroatom selected from —O—, —S—, >SO, >SO$_2$ or >N—COR' where R' is an aliphatic hydrocarbon of 1–17 carbon atoms, —(CH$_2$)$_q$—C$_6$H$_5$ where $q$ is 0 or 1, styryl, diphenyl methyl or phenyl optionally substituted by chlorine, fluorine, methyl and alkoxy having 1–4 carbon atoms. The compound can be prepared by reacting isopropyl aluminate with an ω-diol of the formula

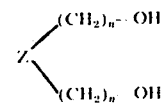

wherein Z has the meaning given above and then reacting the resulting product with dry HCl or an acyl chloride of the formula R'—COCl wherein R' has the meaning given above. The heterocyclic aluminum compound exhibits antiperspirant activity. It can be used in cosmetic antiperspirant compositions comprising a cosmetic vehicle and about 0.2–30 weight percent thereof based on the weight of said composition.

5 Claims, No Drawings

HETEROCYCLIC ALUMINUM COMPOUNDS AND PROCESS FOR THEIR PREPARATION

The present invention relates generally to novel heterocyclic aluminum compounds which are useful as antiperspirants, a process for the preparation thereof, and cosmetic compositions containing the same.

Cosmetic compositions which have a perspiration inhibiting or retarding effect are well known.

Among the most preferred types are those which employ basic aluminum chlorides, more especially, aluminum chlorohydroxide, known commercially as CHLORHYDROL. A certain number of other salts of aluminum, zinc and zirconium have also been proposed, e.g. their phosphates, sulfates, phenosulfonates or methionates. However the antiperspirant activity of these latter salts generally is less than that of CHLORHYDROL, or their toxicity is absolutely unacceptable in cosmetic preparations.

However, a major drawback in the use of basic aluminum chlorides such as aluminum chlorohydroxide is their skin irritant effect. Numerous variants have been proposed to resolve certain technological problems of producing these basic aluminum chlorides and to reduce a certain harshness to the skin that is inherent in their use. For instance, certain derivatives have been proposed such as chlorohydroxyaluminum lactate which is commercially known as CHLORACEL, chlorohydroxyaluminum allantoinate, and even a complex combination of aluminum hydroxychloride with propylene glycol which is commercially known as REHYDROL.

These derivatives have in some cases permitted a reduction of the harshness to the skin of the active substance itself, i.e. aluminum chlorohydroxide, but it has also been observed that there has been a concomitant decrease in activity and often a substantial decrease.

It has now been found that an antiperspirant composition containing the novel heterocyclic aluminum base compounds of the present invention provide excellent antiperspirant activity which, in comparison to presently available compositions containing known antiperspirant compounds, exhibits markedly improved antiperspirancy as well as a significant reduction in any tendency of the composition to irritate the skin.

Thus, the present invention relates to a novel heterocyclic aluminum compound exhibiting highly desirable antiperspirant characteristics, said compound having the formula:

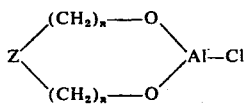 (I)

wherein:
$n$ is 1 or 2, and
a. when $n = 1$, Z represents a —CH=CH— radical; and
b. when $n = 2$, Z is selected from the group consisting of
  i. —$(CH_2)_m$— wherein $m$ is 0–6, and
  ii. a heteroatom, substituted or not, selected from the group consisting of —O—, —S—, >SO, >$SO_2$ and >N-COR′ where R′ is selected from the group consisting of a saturated or unsaturated aliphatic hydrocarbon, branched or not, and having 1 to 17 carbon atoms, —$(CH_2)_q$—$C_6H_5$ wherein $l$ is 0 or 1, styryl, diphenyl methyl and phenyl optionally substituted by a member selected from the group consisting of chlorine, fluorine, methyl, and alkoxy having 1 to 4 carbon atoms.

The compounds of formula I wherein R′ is a saturated or unsaturated aliphatic hydrocarbon include compounds wherein R′ is alkyl of 1 to 17, and preferable 1 to 11 carbon atoms and compounds wherein R′ is alkenyl of 2 to 17, and preferably 2 to 10 carbon atoms.

Representative compounds of formula I include:
1. 2-chloro-4,7-dihydro-1,3,2-dioxalumepine
2. 2-chloro-1,3,2-dioxalumepane
3. 2-chloro-1,3,2-dioxalumonane
4. 2-aluma-1,3-dioxacyclotridecane chloride
5. 2-chloro-1,3,6,2-trioxalumocane
6. 2-chloro-1,3,6,2-dioxathialumocane
7. 2-chloro-6-dodecanoyl-1,3,6,2-dioxazalumocane
8. 6-benzoyl-2-chloro-1,3,6,2-dioxazalumocane
9. 2-chloro-1,3,6,2-S,S-dioxathialumocane dioxide
10. 2-chloro-6-pivaloyl-1,3,6,2-dioxazalumocane
11. 6-p-butoxybenzoyl-2-chloro-1,3,6,2-dioxazalumocane
12. 2-chloro-6-o-methoxybenzoyl-1,3,6,2-dioxazalumocane
13. 2-chloro-1,3,6,2-S-dioxathialumocane oxide
14. 2-chloro-6-diphenylacetyl-1,3,6,2-dioxazalumocane
15. 2-chloro-6-(propene-2-oyl)-1,3,6,2-dioxazalumocane
16. 2-chloro-6-(undecene-9-oyl)-1,3,6,2-dioxazalumocane
17. 2-chloro-6-cinnamoyl-1,3,6,2-dioxazalumocane
18. 2-chloro-6-m-chlorobenzoyl-1,3,6,2-dioxazalumocane
19. 2-chloro-6-o-toluoyl-1,3,6,2-dioxazalumocane The present invention also relates to the process for the preparation of compounds of formula (I). This process comprises reacting aluminum isopropylate with an ω-diol of formula (1) thereby producing a compound of formula (2) which is then isolated or not, to produce the compound of formula (I) above.

This reaction scheme, A, is as follows:

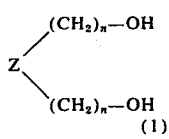 + Al[OCH(CH_3)_2]_3 → 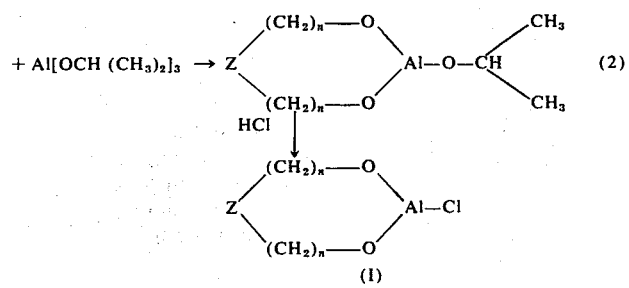

In that instance where, in the compounds of formula (I), Z is >N-COR', these compounds are prepared by initially reacting aluminum isopropylate with an iminodiol of formula (3) to form an aluminum derivative of formula (4) which can then be converted directly to a compound of formula (5) by reaction therewith of an acyl halide of the formula R'COCl.

This reaction scheme, B, is as follows:

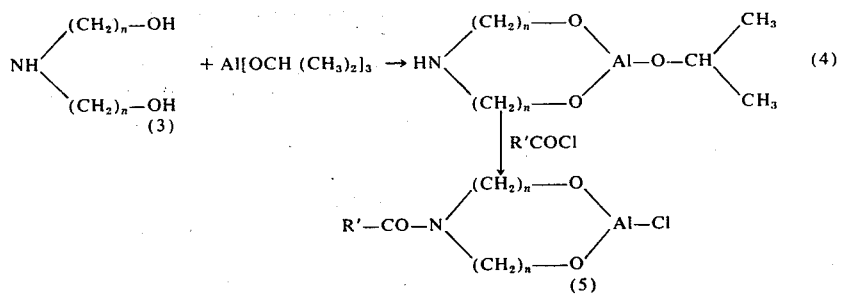

GENERAL REACTION CONDITIONS

The reactions in schemes A and B above are effected in the presence of an anhydrous solvent. Representative of such solvents are aromatic hydrocarbons, such as benzene or toluene; chlorinated hydrocarbons such as methylene chloride, carbon tetrachloride, dichlorethane or chloroform; alcohols such as methanol, ethanol, isopropanol, butanol or isobutanol; and ethers such as ethyl ether, isopropyl ether or dioxane. Preferably the solvent used has a boiling point below 115°C. However, to effect the reaction of a compound of formula (4) (scheme B) with an acyl halide, alcohol solvents are generally avoided.

GENERAL METHODS OF PREPARATION

I. Preparation of the intermediates of formula (2) and (4)

An ω-diol of formula (1) or (3) in solution in an anhydrous solvent ($S_1$) such as those listed above and aluminum isopropylate in solution in an anhydrous solvent ($S_2$) that is identical or different from that employed with the said ω-diol are mixed in equimolecular proportion and heated for about 2 hours at a temperature between about 30° and 80°C.

The resulting reaction mixture includes intermediate products (2) or (4) which can be isolated by evaporation to dryness under reduced pressure and employed in a subsequent reaction (method a, below) or treated directly in the reaction mixture (method b, below).

II. Preparation of chlorinated products (1) and (5)

1. Method (a)
    i. The isolated intermediate product of formula (2) is dissolved or suspended in an anhydrous solvent ($S_3$), such as enumerated above and reacted with an equimolecular amount of dry HCl in solution in an alcohol. After a reaction period of about 30 minutes to 4 hours, the product of formula (I) is isolated by evaporation to dryness under reduced pressure, at a temperature of 50°C or lower. The powders thus obtained include, generally, one-half mole solvation isopropanol.

ii. The isolated intermediate product of formula (4) is added as a solid or as a solution or suspension in an anhydrous solvent (solvent $S_3$), such as those listed above but excluding the alcohols, to an equimolecular quantity of a carboxylic acid chloride of the formula R'COCl in solution in an anhydrous solvent ($S_4$). After a reaction time of about 1 to 48 hours, at a temperature between about 20° to 80° C, the product is isolated by evaporation to dryness under reduced pressure, at a temperature of 80° or lower. The powders thus obtained generally include one-half mole solvation isopropanol.

2. Method (b)
    i. The reaction mixture obtained in the preparation of the compound having formula (2) is reacted directly with an alcohol solution of dry HCl in the same conditions as in method (a)(i). The final product is then isolated in accordance with essentially the same procedures given above.

ii. The reaction mixture obtained in the preparation of the compound having formula (4) is directly reacted with an acyl halide of the formula, R'COCl, optionally, in solution in an anhydrous solvent ($S_4$) under essentially the same conditions as employed in method (a)-(ii). The final product is isolated in accordance with essentially the same procedures given in method (a)-(ii).

The anhydrous solvents employed in the different stages of these reactions can be identical or different. Generally they are selected as a function of the solubilities of the starting products.

The present invention also relates to a cosmetic composition comprising an appropriate cosmetic vehicle and at least one active compound of formula I, as defined above, in amounts of about 0.2 to 30, and preferably from 0.5 to 25, percent by weight of said composition.

The antiperspirant compositions of the invention can be provided in various forms, especially as creams, sticks, powders or even as aerosol sprays.

When the antiperspirant composition of this invention is provided in the form of a cream, the concentration of active compound in the cream is preferably between 0.5 and 20% by weight.

These creams are "oil-in-water" emulsions comprising about 10–30% oil phase and 90–70% water phase. Representative oils, which are readily absorbed by the skin and which are usefully employed as the oil phase of the emulsion include hydrocarbon oils such as paraffin oil, Purcellin oil, perhydrosqualene and solutions of microcrystalline wax in oils; animal or vegetable oils such as sweet almond oil, avocado oil, calophyllum oil, lanolin, castor oil, horse oil, hog oil and olive oil; mineral oils having an initial distillation point at atmospheric pressure of about 250°C and a final point of about 410°C; saturated esters such as isopropyl palmitate, alkyl myristates such as those of isopropyl, butyl and cetyl, hexadecyl stearate, ethyl palmitate, triglycerides of octanoic and decanoic acids, and cetyl ricinoleate.

In the oil phase, it is also possible to use silicone oils that are soluble in other oils, such as dimethylpolysiloxane, methylphenylpolysiloxane and the copolymer, silicone-glycol.

To enhance the retention of the oils, the oil phase can also contain waxes, such as carnauba wax, candellila wax, beeswax, microcrystalline wax and ozokerite.

Fatty alcohols, such as stearyl alcohol, cetyl alcohol, 2-octyl-1-dodecanol, fatty oxyethylene alcohols, propylene glycol and the like can also be used in the cream formulations of the present invention.

When the compositions of the invention are in the form of antiperspirant sticks, the concentration of active compound of formula I, above, is preferably between 0.5 and 10% by weight thereof.

The antiperspirant sticks of the invention are constituted of a fatty excipient such as a molten wax in which there is incorporated, as an emulsion, an aqueous, alcoholic or hydroalcoholic solution of the active antiperspirant compound as defined above. The alcohol is preferably a lower alkanol. It is also possible to introduce into the wax certain amounts of oils and fatty alcohols. Generally the waxes, oils and fatty alcohols used for production of sticks of the invention are the same as those disclosed above in the production of creams.

The emulsifier can be conventional emulsifiers employed for this type of composition. Particularly useful emulsifiers include fatty amides such as coprah monoethanolamide and stearic diethanolamide. The emulsifier will be present in amounts effective to emulsify the aqueous, alcoholic or hydroalcoholic solution of the antiperspirant compound of formula I in the wax and generally in amounts of about 1 to 30 percent by weight of said stick composition.

In the antiperspirant sticks of the present invention, the aqueous, alcoholic or hydroalcoholic solution of the antiperspirant agent represents about 10 to 60% by weight of the stick composition.

When the antiperspirant composition of this invention is in the form of a "compact" powder, the concentration of active antiperspirant compound of formula I is preferably between 5 and 25% by weight of the total weight of the composition. These powder compositions also contain talc or any other similar substance, such as colloidal silica as well as effective amounts of a binding agent such as a fatty substance for instance, sodium stearate, amine stearate, lanolin or vaseline oil to permit agglomeration of the powder. Other conventional binding agents employed in the production of compact powders can be employed.

Preferably, however, the cosmetic antiperspirant composition of the invention is provided as an aerosol spray, which can be alcohol spray or a powder spray, or preferably a dry spray.

In this embodiment of the invention, the concentration of active antiperspirant compound of formula I is generally between 1 and 5% by weight of the total weight of the aerosol composition.

The alcohol spray in aerosol form contains, in addition to the active antiperspirant compound of formula I an anhydrous alcohol selected from the group consisting of ethanol and isopropanol, and at least one liquified propellant, under pressure, such as a halogenated hydrocarbon, including, for instance, dichlorodifluoromethane, trichlorofluoromethane and mixtures thereof.

As in the case of the powders, the dry sprays contain, in addition to the active compound and the pressurized liquid propellant, talc or other similar substances such as colloidal silica, in association with a certain amount of fatty material, e.g. oils, fatty alcohol or saturated esters.

It is understood, of course that all these embodiments, namely creams, sticks and aerosol sprays, may contain any other ingredient generally used in compositions of these types.

In particular, the compositions of the invention may contain preservatives such as methyl para-hydroxybenzoate, or propyl para hydroxybenzoate, perfumes and bactericides such as hexachlorophene, t-butyl hydroxyanisol, propyl gallate, 2'-hydroxy-2,4,4'-trichloro diphenyl ether or di-isobutyl phenoxyethyl dimethylbenzyl ammonium chloride.

By way of illustration, the following examples illustrate the novel heterocyclic aluminum compounds of this invention, their preparation and antiperspirant compositions containing the same.

EXAMPLES 1 – 7

Preparation of 2-chloro-1,3,2-dioxalumepane (Compound 2)

A solution of 90 g 1,4-butanediol in 900 ml methanol is mixed with a solution of 204 g aluminum isopropylate in 900 ml benzene. The resulting mixture is heated at the boil for 2 hours. After cooling, there are then added 192.5 ml of a 5.2 N solution of dry HCl in isopropanol, the resulting mixture then being agitated for 1 hour. After evaporation to dryness under vacuum, at 40°–50°C, a white powder which includes one-half mole solvation isopropanol is obtained, weighing 18.5 g (calculated 18.5 g).

| Analysis | Calculated mEq/g (milliquivalents/gram) | Found mEq/g |
|---|---|---|
| Al | 5.55 | 5.45 |
| Cl | 5.55 | 5.26 |

Proceeding in accordance with the general methods described above, there were also obtained compounds 1, 3, 4, 5, 6, and 13 (see table I).

EXAMPLES 8 – 16

Preparation of 2-m-chloro-6-chlorobenzoyl-1,3,6, 2-dioxazalumocane (Compound 18)

3.78 g of 2-isopropoxy 1,3,6,2-dioxazalumocane are added in portions to an agitated solution of 3.5 g of m-chlorobenzoyl chloride in 20 ml of methylene chloride which is held at 0°C the agitation of the mixture being continued for 4 hours at 5°–10°C. After 12 hours of standing at ambient temperature, the solution is evaporated to dryness under vacuum, at a temperature below 20°C. There are thus obtained 6.67 g of a fine pale yellow powder containing one-half mole of solvation isopropanol.

| Analysis | Calculated mEq/g | Found mEq/g |
|---|---|---|
| Al | 2.99 | 2.98 |
| Cl | 2.99 | 2.98 |

Proceeding in accordance with the above methods there were also obtained compounds 7,8,10,14,15,16,17 and 19 (see Table II).

TABLE I

| Compound | ω-diol (A) of formula (1) | Aluminum Isopropylate (B) | Mole Ratio (A):(B) | Method | Solvents Used ml/Mole of Reactant $S_1$ | $S_2$ | $S_3$ | $S_4$ |
|---|---|---|---|---|---|---|---|---|
| No. 1 | n=1; Z=—CH=CH— | Aluminum Isopropylate | 1:1 | b(i) | Me(800) | Bz(800) | — | — |
| No. 3 | n=2; Z=(CH$_2$)$_m$ with m=2 | Aluminum Isopropylate | 1:1 | b(i) | Me(1000) | Bz(1000) | — | — |
| No. 4 | n=2; Z=(CH$_2$)$_6$ | Aluminum Isopropylate | 1:1 | b(i) | Me(1000) | Bz(1000) | — | — |
| No. 5 | n=2; Z=—O— | Aluminum Isopropylate | 1:1 | a(i) | Me(1000) | Bz(1500) | Et(2000) | — |
| No. 6 | n=2; Z=—S— | Aluminum Isopropylate | 1:1 | b(i) | Ch(250) | Ch(375) | — | — |
| No. 13 | n=2; Z=>SO | Aluminum Isopropylate | 1:1 | b(i) | Is(2000) | Is(1000) | — | — |

| Compound | Reaction Conditions Temp °C | Time- Hours | Yield g/mole of Reactants Calculated | Found | Analysis Al mEq/g Calculated | Found | Cl mEq/g Calculated | Found |
|---|---|---|---|---|---|---|---|---|
| No. 1 | 25 | 1 | 178.5 | 179 | 5.6 | 5.55 | 5.6 | 5.22 |
| No. 3 | 40 | 0.5 | 208.5 | 202 | 4.8 | 4.85 | 4.8 | 4.46 |
| No. 4 | 35 | 1 | 264.5 | 270 | 3.78 | 3.61 | 3.78 | 3.52 |
| No. 5 | 20 | 4 | 196.5 | 200 | 5.08 | 5.04 | 5.08 | 4.70 |
| No. 6 | 40 | 1 | 212.5 | 213.5 | 4.75 | 4.62 | 4.75 | 4.70 |
| No. 13 | 25 | 1 | 114.7 | 121 | 4.37 | 4.12 | 4.37 | 4.05 |

Key:
Me=methanol
Ch=Chloroform
Is=Isopropanol
Bz=benzene

TABLE II

| Compound | Iminodiol (A) of formula (3) | Aluminum Isopropylate (B) → (C) | Mole Ratio (A):(B) | Carboxylic Acid Chloride R'COCl (D) | Mole Ratio (C):(D) | Method | Solvents $S_3$ | $S_4$ |
|---|---|---|---|---|---|---|---|---|
| No. 10 | n = 2 | Aluminum Isopropylate | 1:1 | pivaloyl chloride | 1:1 | b(ii) | — | CH$_2$Cl$_2$ |
| No. 14 | n = 2 | Aluminum Isopropylate | 1:1 | diphenyl acetyl chloride | 1:1 | b(ii) | — | CH$_2$Cl$_2$ |
| No. 15 | n = 2 | Aluminum Isopropylate | 1:1 | propene-2-oyl chloride | 1:1 | b(ii) | — | CH$_2$Cl$_2$ |
| No. 16 | n = 2 | Aluminum Isopropylate | 1:1 | undecene-9-oyl chloride | 1:1 | b(ii) | — | CH$_2$Cl$_2$ |
| No. 17 | n = 2 | Aluminum Isopropylate | 1:1 | cinnamoyl chloride | 1:1 | b(ii) | — | CH$_2$Cl$_2$ |
| No. 19 | n = 2 | Aluminum Isopropylate | 1:1 | o-toluoyl chloride | 1:1 | b(ii) | — | CH$_2$Cl$_2$ |
| No. 7 | n = 2 | Aluminum Isopropylate | 1:1 | dodecanoyl chloride | 1:1 | a(ii) | benzene | benzene |
| No. 8 | n = 2 | Aluminum Isopropylate | 1:1 | benzoyl chloride | 1:1 | a(ii) | benzene | benzene |

| Compound | Reaction Conditions Temp °C | Time- Hours | Yield (grams) Calculated | Found | Analysis Al mEq/g Calculated | Found | mEq/g Calculated | Found |
|---|---|---|---|---|---|---|---|---|
| No. 10 | −10° | 2 | 5.6 | 5.6 | 3.58 | 3.58 | 3.58 | 3.52 |
| No. 14 | −10° | 4 | 7.9 | 7.95 | 2.57 | 2.51 | 2.57 | 2.39 |
| No. 15 | 25° | 3 | 12.4 | 12.0 | 4.00 | 4.02 | 4.00 | 4.00 |
| No. 16 | 10° | 4 | 7.4 | 7.3 | 2.77 | 2.71 | 2.77 | 2.63 |
| No. 17 | 5° | 48 | 6.5 | 6.7 | 3.07 | 2.98 | 3.07 | 2.84 |
| No. 19 | 5° | 3 | 6.25 | 6.2 | 3.19 | 3.19 | 3.19 | 3.13 |
| No. 7 | 80° | 2 | 377.5* | 370* | 2.65 | 2.64 | 2.65 | 2.66 |

TABLE II-continued

| Compound | Iminodiol (A) of formula (3) | Aluminum Isopropylate (B) | (C) | Mole Ratio (A):(B) | Carboxylic Acid Chloride R'COCl (D) | Mole Ratio (C):(D) | Method | Solvents $S_3$ | $S_4$ |
|---|---|---|---|---|---|---|---|---|---|
| No. 8 | 40° | 18 | | 299.5* | 301* | 3.35 | 3.25 | 3.35 | 3.44 |

*Yield in g/mole of reactants

EXAMPLE 17

An antiperspirant cream, in accordance with the present invention is prepared by admixing the following components:

| | | |
|---|---|---|
| stearyl alcohol oxyethylenated with 15 moles ethylene oxide per mole alcohol | 12 | g |
| spermaceti wax | 4 | g |
| isopropyl myristate | 3 | g |
| silicone oil (density at 25°C = 1.05 – 1.08 refraction index 1.485–1.495) | 0.5 | g |
| methyl para hydroxybenzoate | 0.1 | g |
| propyl para hydroxybenzoate | 0.1 | g |
| propylene glycol | 2 | g |
| 2-chloro-4,7-dihydro-1,3,2-dioxalumepine (compound No. 1) | 2 | g |
| perfume | 0.5 | g |
| water, q.s.p. | 100 | g |

This example is repeated except that essentially equivalent amounts of compound 9 are used instead of compound 1.

EXAMPLE 18

An antiperspirant stick, in accordance with the present invention, is prepared by admixing the following components:

| | | |
|---|---|---|
| stearyl alcohol | 10 | g |
| microcrystalline wax | 4 | g |
| paraffin oil | 10 | g |
| coprah monoethanolamide | 10 | g |
| stearic diethanolamide | 10 | g |
| 2-octyl-1-dodecanol | 10 | g |
| propylene glycol | 20 | g |
| ethyl alcohol | 20 | g |
| perfume | 1 | g |
| 2-aluma-1,3-dioxacyclotridecane chloride (compound No. 4) | 5 | g |

This example is repeated except that compound No. 4 is replaced by essentially equivalent amounts of compound No. 12.

EXAMPLE 19

An antiperspirant stick, in accordance with the present invention, is prepared by admixing the following components:

| | | |
|---|---|---|
| stearic diethanolamide | 5 | g |
| mixture comprising 30% cetyl alcohol and 70% stearyl alcohol, the whole oxyethylenated with 13 moles ethylene oxide per mole alcohol of the mixture | 10 | g |
| water | 20 | g |
| microcrystalline wax | 5 | g |
| paraffin oil | 10 | g |
| perhydrosqualene | 3 | g |
| beeswax | 5 | g |
| ethyl alcohol | 36 | g |
| 2-chloro-1,3,6,2-trioxalumocane (compound No. 5) | 5 | g |
| perfume | 1 | g |

This example is repeated except that compound No. 5 is replaced with essentially equivalent amounts of compound No. 10.

EXAMPLE 20

An alcohol-based antiperspirant spray in accordance with the present invention is prepared by admixing the following components:

| | | |
|---|---|---|
| hexachlorophene | 0.1 | g |
| 6-benzoyl-2-chloro-1,3,6,2-dioxazalumocane (compound No. 8) | 5.2 | g |
| perfume | 1 | g |
| ethyl alcohol | 93.7 | g |

50 g of this mixture are then packaged, under pressure, in an aerosol container together with 50 g dichlorodifluoromethane as the aerosol propellant.

EXAMPLE 21

An alcohol-based antiperspirant spray, in accordance with the present invention is prepared by admixing the following components:

| | | |
|---|---|---|
| propyl gallate | 0.2 | g |
| 6-benzoyl-2-chloro-1,3,6,2-dioxazalumocane (compound No. 8) | 3.5 | g |
| perfume | 0.5 | g |
| ethyl alcohol | 95.8 | g |

55 g of this mixture are then packaged under pressure in an aerosol container together with 45 g dichlorodifluoromethane as the aerosol propellant.

This example is repeated except that compound No. 8 is replaced with essentially equivalent amounts of compound No. 15.

EXAMPLE 22

A dry antiperspirant spray, in accordance with the present invention is prepared by admixing the following components:

| | | |
|---|---|---|
| 2-chloro-1,3,2-dioxalumepane (compound No. 2) | 35 | g |
| colloidal silica | 3 | g |
| perfume | 7 | g |
| isopropyl palmitate, q.s.p. | 100 | g |

10 g of this mixture are then packaged under pressure in an aerosol container together with a mixture of 45 g dichlorodifluoromethane and 45 g trichlorofluoromethane, as the aerosol propellant.

This example is repeated except that compound No. 2 is replaced with essentially equivalent amounts of compound No. 18.

EXAMPLE 23

A dry antiperspirant spray in accordance with the present invention is prepared by admixing the following components:

| | |
|---|---|
| 2-chloro-1,3,2-dioxalumonane (compound No. 3) | 35 g |
| colloidal silica | 3 g |
| perfume | 7 g |
| $C_8 - C_{12}$ fatty acid triglycerides, q.s.p. | 100 g |

10 g of this mixture are then packaged under pressure in an aerosol container together with a mixture of 45 g trichlorofluoromethane and 45 g dichlorodifluoromethane as the aerosol propellant.

This example is repeated except that compound No. 3 is replaced with essentially equivalent amounts of compound No. 11.

EXAMPLE 24

A dry, impalpable antiperspirant spray, in accordance with the present invention, is prepared by admixing the following components:

| | |
|---|---|
| 2-chloro-1,3,6,2-dioxathialumocane (compound No. 6) | 3.5 g |
| 2'-hydroxy-2,4,4'-trichloro diphenyl ether | 0.1 g |
| talc | 0.3 g |
| perfume | 0.2 g |
| isopropyl palmitate | 1.2 g |
| trichlorofluoromethane | 47.35 g |
| dichlorodifluoromethane | 47.35 g |

The above composition is packaged, under pressure, in an aerosol container.

This example is repeated except that compound No. 6 is replaced with essentially equivalent amounts of compound No. 19.

EXAMPLE 25

An impalpable, dry antiperspirant spray in accordance with the present invention is prepared by admixing the following components:

| | |
|---|---|
| 2-chloro-4,7-dihydro-1,3,2-dioxalumepine (compound No. 1) | 3.5 g |
| diisobutylphenoxy ethoxyethyl dimethylbenzyl ammonium chloride | 0.1 g |
| perfume | 0.2 g |
| ester of starch (starch reticulated with adipic acid) | 0.3 g |
| silicone oil | 1.2 g |
| trichlorofluoromethane | 47.35 g |
| dichlorodifluoromethane | 47.35 g |

The above composition is packaged, under pressure, in an aerosol container.

This example is repeated except that compound No. 1 is replaced with essentially equivalent amounts of compound No. 17.

EXAMPLE 26

A dry antiperspirant spray, in accordance with the present invention, is prepared by admixing the following components:

| | |
|---|---|
| sorbitan trioleate (viscosity at 25°C = 250 cps, HLB = 1.8) | 4 g |
| isopropyl myristate | 6.5 g |
| deodorized kerosene | 8 g |
| polyethylene glycol (M.W. 400) | 4 g |
| colloidal silica | 4 g |
| perfume | 1 g |
| 2-chloro-1,3,2-dioxalumonane (compound No. 3) | 20 g |
| microtalc (5 microns) | 52 g |

10 g of this mixture are packaged in an aerosol container together with a mixture of 45 g of trichlorofluoromethane and 45 g of dichlorodifluoromethane as the aerosol propellant.

This example is repeated except that compound No. 3 is replaced with essentially equivalent amounts of compound No. 13.

EXAMPLE 27

A deodorant antiperspirant spray talc in accordance with the present invention is prepared by admixing the following components:

| | |
|---|---|
| sorbitan trioleate | 4 g |
| isopropyl myristate | 6.5 g |
| deodorized kerosene | 8 g |
| polyethylene glycol (M.W. = 400) | 4 g |
| colloidal silica | 4 g |
| microtalc (5 microns) | 22.5 g |
| perfume | 1 g |
| 2-chloro-1,3,2-diolaxumepane (compound No. 2) | 50 g |

10 g of this mixture are packaged under pressure in an aerosol container together with a mixture of 45 g of trichlorofluoromethane and 45 g of dichlorodifluoromethane, as the aerosol propellant.

This example is repeated except that compound No. 2 is replaced by essentially equivalent amounts of compound No. 14.

EXAMPLE 28

A compact powder antiperspirant composition in accordance with the present invention is prepared by admixing the following components:

| | |
|---|---|
| talc | 70 g |
| lanolin | 2.5 g |
| oil of vaseline | 2 g |
| perfume | 0.5 g |
| 2-chloro-1,3,6,2-trioxalumocane (compound No. 5) | 25 g |

This example is repeated except that compound No. 5 is replaced by essentially equivalent amounts of compound No. 16.

EXAMPLE 29

A dry antiperspirant spray in accordance with the present invention is prepared by admixing the following components:

| | |
|---|---|
| p,p'(hexamethylenedioxy) dibenzamidinium diisethionate | 0.1 g |
| 2-chloro-1,3,2-dioxalumonane (compound No. 3) | 30 g |
| colloidal silica | 2.5 g |
| perfume | 5 g |
| $C_8 - C_{12}$ fatty acid triglycerides, q.s.p. | 100 g |

15 g of this mixture are packaged in an aerosol container together with a mixture of 30 g of trichlorofluoromethane and 55 g of dichlorodifluoromethane as the aerosol propellant.

What is claimed is:

1. A compound of the formula

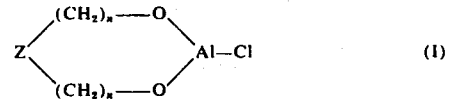

(I)

wherein:

n is 1 or 2, and
a. when $n = 1$, Z is —CH=CH—; and
b. when $n = 2$, Z is selected from the group consisting of
   i. —(CH$_2$)$_m$ wherein m is 0–6, and
   ii. a heteroatom, optionally substituted, selected from the group consisting of —O—, —S—, >SO, >SO$_2$ and >N-COR' wherein R' is selected from the group consisting of aliphatic hydrocarbon, saturated or unsaturated, branched or straight chain, having 1 to 17 carbon atoms, —(CH$_2$)$_q$—C$_6$H$_5$ wherein q is 0 or 1, styryl, diphenyl methyl and phenyl optionally substituted by a member selected from the group consisting of chlorine, fluorine, methyl and alkoxy having 1 to 4 carbon atoms.

2. A compound of claim 1, selected from the group consisting of
1. 2-chloro-4,7-dihydro-1,3,2-dioxalumepine,
2. 2-chloro-1,3,2-dioxalumepane,
3. 2-chloro-1,3,2-dioxalumonane,
4. 2-aluma-1,3-dioxacyclotridecane chloride,
5. 2-chloro-1,3,6,2-trioxalumocane,
6. 2-chloro-1,3,6,2-dioxathialumocane,
7. 2-chloro-6-dodecanoyl-1,3,6,2-dioxazalumocane,
8. 6-benzoyl-2-chloro-1,3,6,2-dioxazalumocane,
9. 2-chloro-1,3,6,2-S,S-dioxathialumocane dioxide,
10. 2-chloro-6-pivaloyl-1,3,6,2-dioxazalumocane,
11. 6-p-butoxybenzoyl-2-chloro-1,3,6,2-dioxazalumocane,
12. 2-chloro-6-o-methoxybenzoyl-1,3,6,2-dioxazalumocane,
13. 2-chloro-1,3,6,2-S-dioxathialumocane oxide,
14. 2-chloro-6-diphenylacetyl-1,3,6,2-dioxazalumocane,
15. 2-chloro-6-(propene-2-oyl)-1,3,6,2-dioxazalumocane,
16. 2-chloro-6-(undecene-9-oyl)-1,3,6,2-dioxazalumocane,
17. 2-chloro-6-cinnamoyl-1,3,6,2-dioxazalumocane,
18. 2-chloro-6-m-chlorobenzoyl-1,3,6,2-dioxazalumocane and
19. 2-chloro-6-o-toluoyl-1,3,6,2-dioxazalumocane.

3. A process for the preparation of the compound of claim 1, comprising reacting in an anhydrous solvent and in essentially equimolar amounts (i) an ω-diol of the formula:

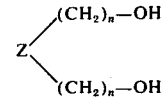

wherein n is 1 or 2 and (a) when $n = 1$, Z represents —CH=CH— and (b) when $n = 2$, Z is selected from the group consisting of —(CH$_2$)$_m$ wherein $m = 0$–6 and a hetero atom selected from the group consisting of —O—, —S—, >SO, >SO$_2$ and >NH, with (ii) aluminum isopropylate, and reacting the product resulting from the reaction with a member selected from the group consisting of (1) dry hydrochloric acid when Z is other than >NH and (2) acyl halide of the formula R'—COCl when Z is >NH, wherein R' has the meaning given in claim 1.

4. The process of claim 3 wherein said anhydrous solvent is selected from the group consisting of aromatic hydrocarbon, chlorinated hydrocarbon, alcohol, ether and mixtures thereof.

5. 2-chloro-1,3,6,2-dioxathialumocane, as claimed in claim 1.

* * * * *